United States Patent [19]

Thomas, III et al.

[11] Patent Number: 5,457,863
[45] Date of Patent: Oct. 17, 1995

[54] METHOD OF MAKING A TWO DIMENSIONAL ULTRASONIC TRANSDUCER ARRAY

[75] Inventors: Lewis J. Thomas, III; Lowell S. Smith, Schenectady, both of N.Y.

[73] Assignee: General Electric Company, Schenectady, N.Y.

[21] Appl. No.: 34,992

[22] Filed: Mar. 22, 1993

[51] Int. Cl.⁶ .................................................. H01L 41/22
[52] U.S. Cl. ........................................... 29/25.35; 310/334
[58] Field of Search .................. 29/25.35; 310/334–337, 310/327

[56] References Cited

U.S. PATENT DOCUMENTS 4,783,888  11/1988  Fujii et al. .............................. 29/25.35
4,825,115   4/1989  Kawabe et al. .................... 29/25.35 X

OTHER PUBLICATIONS

"Ultrasound Imaging: An Overview", Hewlett–Packard Journal, Oct., 1983.

Primary Examiner—Carl E. Hall
Attorney, Agent, or Firm—Paul R. Webb, II

[57] ABSTRACT

An improved two-dimensional ultrasonic transducer array is provided by forming a plurality of elongated transducer strips each including a central body of piezoelectric material having mounted thereon a conducting inner matching layer and outer matching layer, a conducting inner backing layer and a nonconducting lossy outer backing layer, depositing a conducting film on the outer surface and one side surface of the outer matching layer and into electrical contact with the conducting backing layer of each strip and depositing a plurality of conducting films in space relation to one another on the back surface and one side surface of the lossy backing layer and into electrical contact with the conducting backing layer to provide an electric circuit to the front and back faces of the piezoelectric layer. The strips are then assembled in spaced parallel relation with insulating strips bonded therebetween, and grooves are cut transversely of the transducer strip through the matching layers, the piezoelectric layer, the inner backing layer and into but not through the lossy backing layer to thereby provide an array of individual transducers arranged in spaced parallel rows with conducting films extending from the face and back surfaces of each transducer to provide an independent electrical circuit to each transducer in the array.

11 Claims, 4 Drawing Sheets

METHOD OF MAKING A TWO DIMENSIONAL ULTRASONIC TRANSDUCER ARRAY

BACKGROUND OF THE INVENTION

1. Field of the Invention

This invention relates to ultrasonic transducers, and more particularly to an improved two-dimensional ultrasonic transducer and its method of construction.

2. Description of the Prior Art

Ultrasonic transducers of the type currently widely used in the medical field for imaging commonly employ a one-dimensional transducer array, i.e., an array of ultrasonic transducer elements wherein the outgoing sound pulses can be steered and dynamically focused in one direction only. Transducers employing two-dimensional arrays are also known but are not believed to be commercially available despite the increased advantages and the flexibility of use provided by a two-dimensional array.

One problem in developing a commercially feasible two-dimensional ultrasonic transducer array has been the difficulty in providing electrical connections to the individual transducer elements, particularly the connections at the front of the transducer, i.e., the transducer face from which the sound is emitted. Additionally, the relatively high number of individual transducer elements involved in a practical two-dimensional array requires a correspondingly large number of electronic elements for individually driving the respective transducer elements for steering and focusing the beam. Developments in the electronic controls have been made, however, which make it feasible to control a two-dimensional phased array having sufficient transducer elements to provide effective imaging.

The typical ultrasonic transducer used for imaging in the medical field employs a body of piezoelectric material such as PZT sandwiched between one or more backing layers and one or more matching layers. Electric current is provided to the piezoelectric material through conductive ribbons such as thin metal films or polymer films having a coating of conductive metal deposited thereon with the ribbons being attached to the front and back face of the piezoelectric layer before the matching and backing layers are attached. Preferably the piezoelectric body is electroded on its front and back surfaces to assure good electrical connections with the conductive ribbons. The conductive ribbons are routed out the side of the finished transducer for connection to a suitable power supply. One-dimensional arrays of this type may be constructed by initially building a large transducer block having sheets of the conductive film attached to the front and back faces, respectively, of the piezoelectric material, then cutting or sawing the block through the matching layer, piezoelectric layer and attached conductive films, and partially through the backing layer to thereby form an array of spaced parallel transducer elements with the severed conductive ribbon strips providing electrical connection to the back and front faces of the piezoelectric material of each transducer element in the array. In this arrangement, the conductive strips or ribbons extend from the ends of the individual elongated transducer elements in much the same manner as in a single element transducer.

In a two-dimensional transducer array where a plurality of individual transducer elements are arranged in spaced rows extending both longitudinally and transversely to the assembly, it is apparent that the relatively simple current supply system described above cannot be employed to provide power to all the individual transducers in the array. The connections to the back of the transducers in such a two-dimensional array present a particular difficulty because of the necessity to isolate the individual transducers from one another to avoid interference with the sound transmitted by surrounding transducer elements. Accordingly, it is a primary object of the present invention to provide an improved method of producing a two-dimensional ultrasonic transducer array and to an improved ultrasonic transducer array produced by the method.

Another object is to provide an improved method of producing a two-dimensional ultrasonic transducer array including an improved conductor system for providing electrical connections to the piezoelectric element of each transducer while avoiding both electrical and mechanical interference with surrounding transducers.

Another object is to provide an improved two-dimensional ultrasonic transducer array in which the transducer elements are arranged in parallel rows each consisting of a plurality of individual transducer elements, with the rows extending in two directions substantially perpendicular to one another, and to an improved method of producing such a two-dimensional ultrasonic transducer array.

SUMMARY OF THE INVENTION

In the attainment of the foregoing and other objects and advantages of the invention, an important feature resides in initially constructing a relatively large transducer block comprising a single generally rectangular piezoelectric body having two layers of backing material including an inner electrically conducting layer and an outer lossy backing layer attached to its back surface and two layers of matching material including an inner electrically conducting layer attached to its front surface. The transducer block is then cut or sawed in spaced parallel planes perpendicular to the layers to form a plurality of substantially identical, elongated, relatively narrow transducer strips each comprising an elongated piezoelectric body having two backing layers and two matching layers attached thereto.

Electrical connections to the front and back faces of the piezoelectric material are provided by metal films formed on the outer face of the outer matching layer and the outer backing layer, with the films extending over the edge and along one cut surface of the matching and backing layers. The metal film provided on the front face and edge surfaces of the matching layers to provide connection to the front face of the piezoelectric layer may be a continuous film, while the film provided on the back and edge surfaces of the backing layers is in the form of spaced strips each located to provide electrical connection to the piezoelectric layer of a single transducer element in the final array while maintaining electrical isolation between adjacent transducer elements. The conducting films preferably are metal films formed by a vapor deposition, ion sputtering, electroless plating or electrolysis plating operation.

After the conducting films are formed on the transducer strips, the strips are again assembled into a block form, and grooves or kerfs are cut from the front face through the matching layers, the piezoelectric body, the electrically conducting backing layer, and into but not completely through the outer lossy backing layer. The saw kerfs sever the conducting film on the face of the strips into individual conductor elements each providing electrical contact from the outer surface of the outer matching layer to the inner electrically conducting matching layer which is in electrical contact with the face of the piezoelectric body of the associated transducer element formed by the grooving operation.

The individual transducer strips having the transverse grooves formed therein are next separated and reassembled with a suitable electrically insulating spacer element contacting the backing layers, or the outer backing layer of adjacent strips, and a suitable bonding material is employed to join the transducer strips into a block form so that the individual transducer elements are equally spaced longitudinally and transversely to the array. The air gaps provided by the saw kerfs or grooves and by the spacer elements isolate the respective transducer elements in the array.

Electric current is provided to the back of the piezoelectric layer of each transducer element by bonding a separate conductor to each of the isolated patches of metal film on the back surface of the backing lossy layer. Power may be supplied by attaching the array to a printed circuit board having electronic components for driving the individual transducer in the array. Contact with the front of the array may be achieved by providing a thin conductive film such as a metallized polymer film which extends over and provides electrical contact with the front surface of all the transducer elements in the array. This film also provides a membrane seal for the complete array, preventing fluids or other matter from entering the air gaps isolating the individual transducer elements.

BRIEF DESCRIPTION OF THE DRAWINGS

Other features and advantages of the invention will be apparent from the detailed description contained hereinbelow, taken in conjunction with the drawings in which.

DESCRIPTION OF THE PREFERRED EMBODIMENTS

Figure 1:
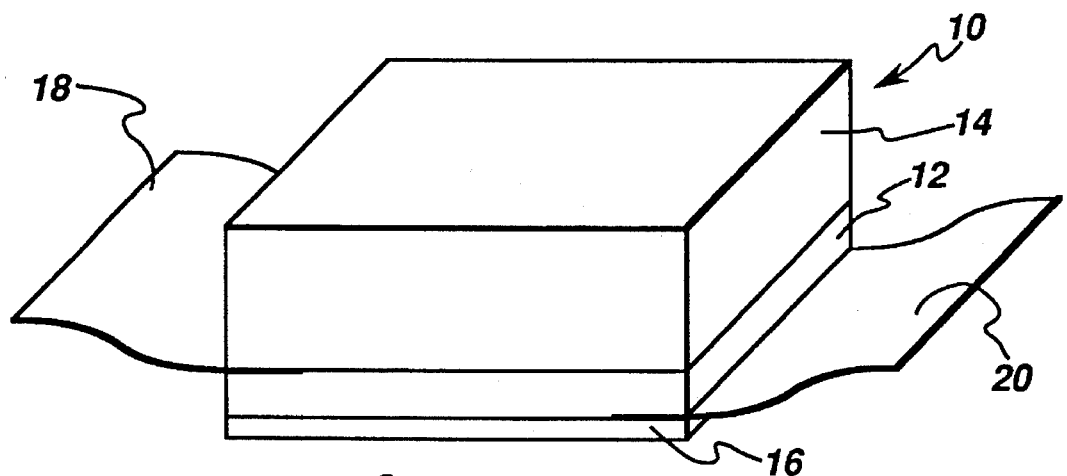
FIG. 1 is an isometric view schematically showing a transducer block used in the production of a prior art one-dimensional ultrasonic transducer array.
Figure 2:
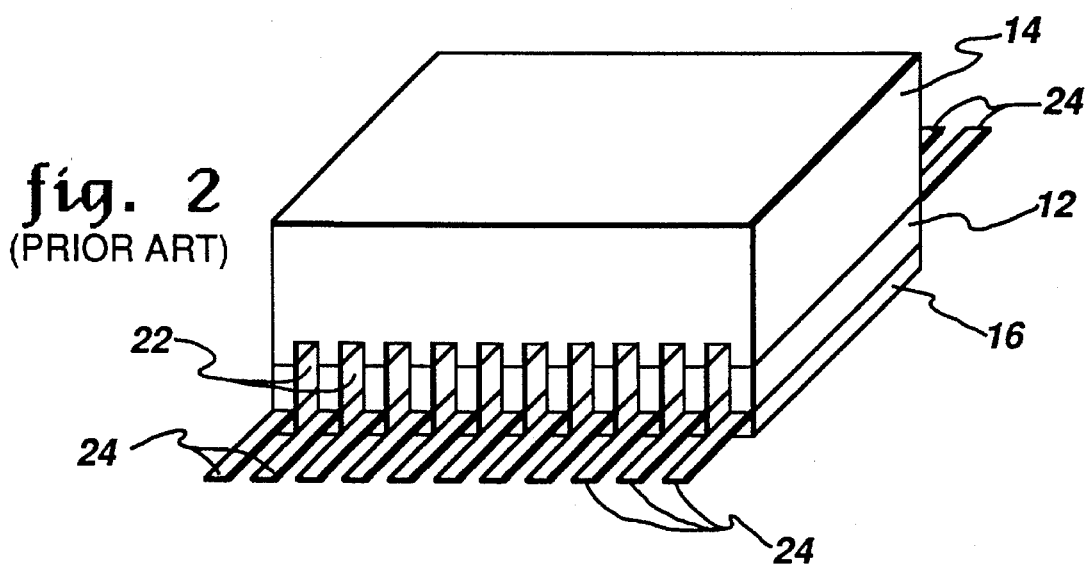
FIG. 2 is an isometric view schematically illustrating a prior art one-dimensional transducer array.

Referring now to the drawings in detail, a prior art one-dimensional ultrasonic transducer and its method of construction will be briefly described with reference to FIGS. 1 and 2. Such known one-dimensional arrays may be formed by initially producing a relatively large, generally rectangular transducer block assembly designated generally by the reference numeral 10 in FIG. 1. Block 10 comprises a layer of piezoelectric material 12 sandwiched between and bonded to a single lossy backing layer 14 and a single matching layer 16. A conducting film 18 such as a thin sheet of metal or a film of polymer material having a thin coating of conductive metal deposited on one side thereof is attached to the back surface of the piezoelectric material at least along one full edge thereof, and a second such conducting film 20 is attached to the front face of the piezoelectric material at least along the one full edge thereof parallel to second one full edge of second back surface. The conducting films are secured to the piezoelectric layer before the matching and backing layers are attached and are firmly retained in position by the backing and matching layers respectively. The conducting films extend outwardly from the transducer block as illustrated in FIG. 1 for easy connection to a power source.

After assembly of the transducer block 10, a plurality of spaced parallel grooves 22 are milled or sawed into the front surface or face of the block, i.e., the surface from which the sound is emitted, with the grooves 22 extending completely through the matching layer, the piezoelectric body and conductive films, and into but not through the lossy backing layer to produce a plurality of individual, elongated parallel transducers spaced from one another by the width of the groove and supported on the common lossy backing layer. By severing the projecting ends of the sheets of conductive film into a plurality of ribbons 24 during the milling or sawing operation, the piezoelectric layer of each individual elongated transducer has a ribbon 24 attached to its front and back surfaces to provide an electric circuit to the piezoelectric material.

The individual transducer elements of the single dimension transducer assembly may be connected to appropriate electronics for control as a phased array and electronically controlled to steer and focus the emitted ultrasonic beam in a known manner. As explained hereinabove, however, such a single dimension phase array can be steered and focused in one direction only and for many uses, a two-directional phase array would be desirable so that the beam could be steered and focused in two directions perpendicular to one another.

A two-dimensional phased array ultrasonic transducer employs a plurality of individual elements arranged in rows extending in two directions, normally perpendicular to one another. Thus, it is apparent that the power supply system described above with regard to a single dimension array cannot be employed to provide individually controlled electrical circuits to each of the transducer elements in such a two-dimensional array. Further, accurate control of such a two-dimensional array requires isolation of the individual transducers so that, from a practical standpoint, leads cannot extend within the grooves between adjacent transducer elements.

As is known, the function of the matching layer of an ultrasonic transducer is to provide efficient transfer of acoustic energy across the interface between the piezoelectric element and the coupling medium, or sample. Assuming that the piezoelectric material is PZT having an acoustical impedance of approximately 30 MRayls, and the device is to be coupled to water having an acoustical impedance of 1.5 MRayls or to the human body having a similar impedance, the matching layer should have an impedance of approximately 6.7 MRayls. Such an acoustical impedance may be difficult to achieve and it is common to use two matching layers. In such a two matching layer arrangement, one matching layer normally will have an impedance greater than that required for a single matching layer and be located adjacent the PZT material, while the second matching layer will have a lower impedance so that the combined layers provide the desired matching impedance. In the transducer array according to the present invention, two matching layers and two backing layers are employed, with the matching and backing layers contacting the piezoelectric layer being an electrically conducting material, preferably metal.

Figure 3:
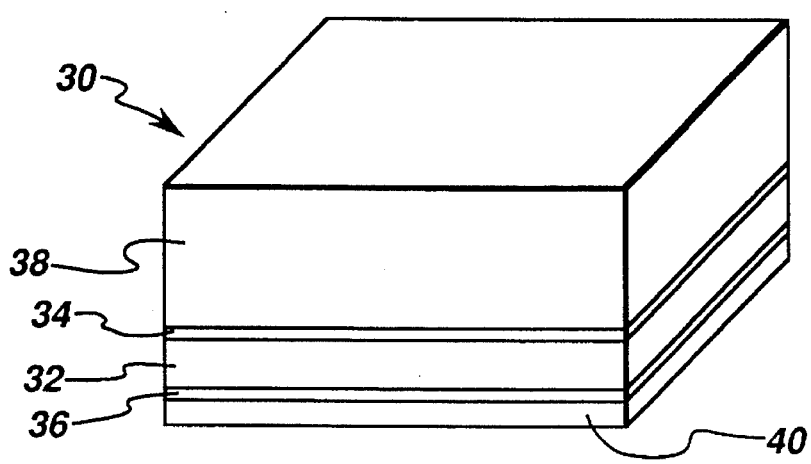
FIG. 3 is an isometric view similar to FIG. 1 and schematically showing a transducer block assembled as an initial step of the process of the present invention.

As the initial step in constructing the two-dimensional transducer array according to the present invention, a large rectangular transducer block indicated generally at 30 is constructed much in the same manner as described above with reference to FIGS. 1 and 2, except that the conducting films are omitted. Again the piezoelectric body preferably has an electrically conductive metal coating on its front and back surfaces. Referring first to FIG. 3, it is seen that block 30 comprises a layer 32 of piezoelectric material having a metal backing layer 34 bonded to and providing electrical contact with its back surface and a metal matching layer 36 bonded to and providing electrical contact with its face or front surface. A thicker layer of lossy backing material 38 is bonded to layer 34, and an outer matching layer 40 of synthetic resin material is bonded to the front face of the metal matching layer 36.

Figure 4:
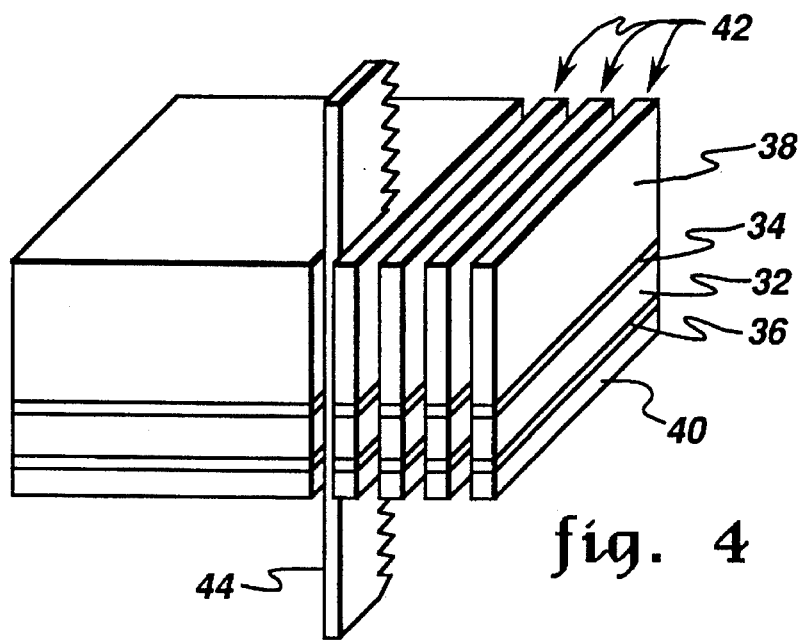
FIG. 4 is a view similar to FIG. 3 and showing the transducer block of FIG. 3 being sawed into elongated thin transducer strips.
Figure 5:
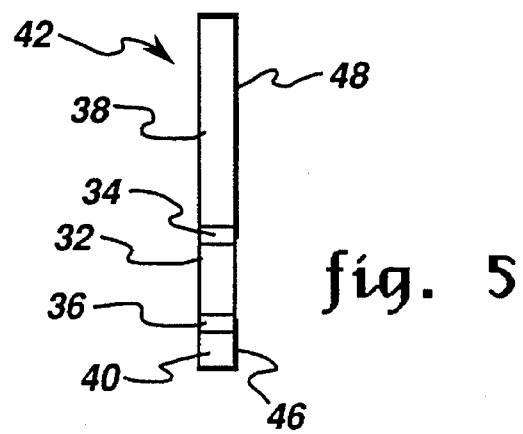
FIG. 5 is an end elevation view of one of the transducer strips having electrically conducting films formed thereon.
Figure 6:
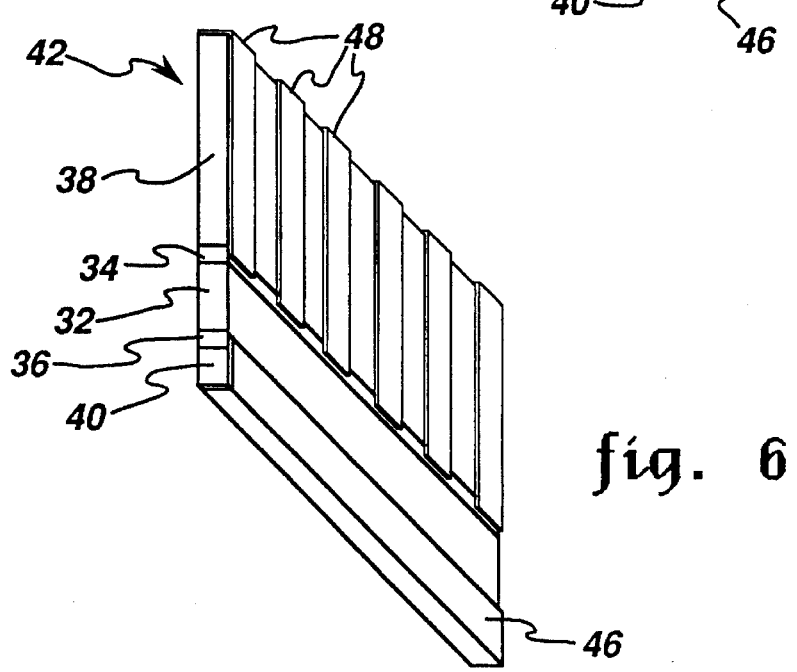
FIG. 6 is an isometric view showing the back and side of the transducer strip shown in FIG. 5.
Figure 7:
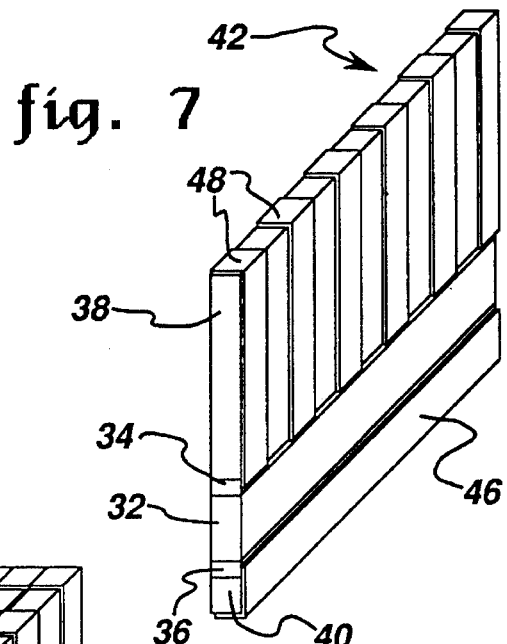
FIG. 7 is an isometric view showing the front and side of the transducer strip shown in FIGS. 5 and 6.

As shown in FIG. 4, the transducer block 30 is then cut, perpendicular to the layers, into a plurality of equally dimensioned transducer strips 42, using any suitable cutting means indicated schematically in FIG. 4 by the saw blade 44.

A conductive metal film 46 is formed on and extends over the front face of the outer matching layer 36 and along the side edges of the matching layers 36, 40 of the respective strips 42 to provide an electric circuit to the front face of the piezoelectric layer 32. Layer 46 covers the entire front face and one side edge surface of the outer matching layer and extends into overlying relation and provides electrical contact with the inner or metal matching layer 46 to thereby provide electrical contact with the front face of the piezoelectric layer 32 along the full length of each strip 42.

A plurality of equally spaced conductive metal film strips 48 are also provided along the length of the transducer strips 42, with the film strips 48 each extending transversely across the outer or back face of the lossy backing layer 38 and over one edge of this layer into overlying relation with the metal backing layer 36 to thereby provide electrical contact with the back surface of the piezoelectric layer 32 at spaced intervals along its length. Conductive films 46 and 48 are preferably coated directly onto the supporting elements of the transducer strips 42 by a suitable process such as by a vapor deposition, ion sputtering, electroless plating or electrolysis plating process.

Figure 8:
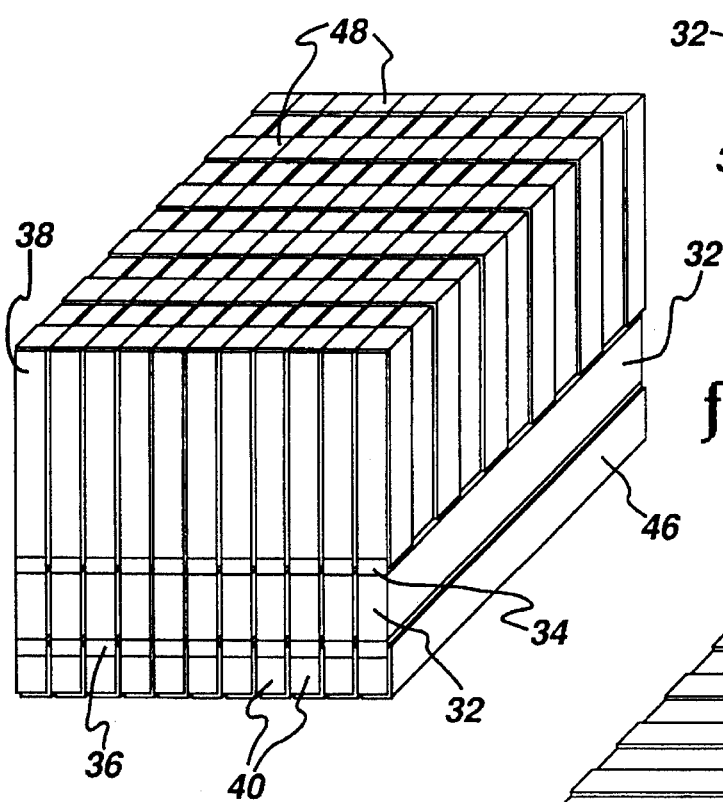
FIG. 8 is an isometric view of the transducer strips having thin conductor films thereon reassembled in side-by-side relation to form a block.
Figure 9:
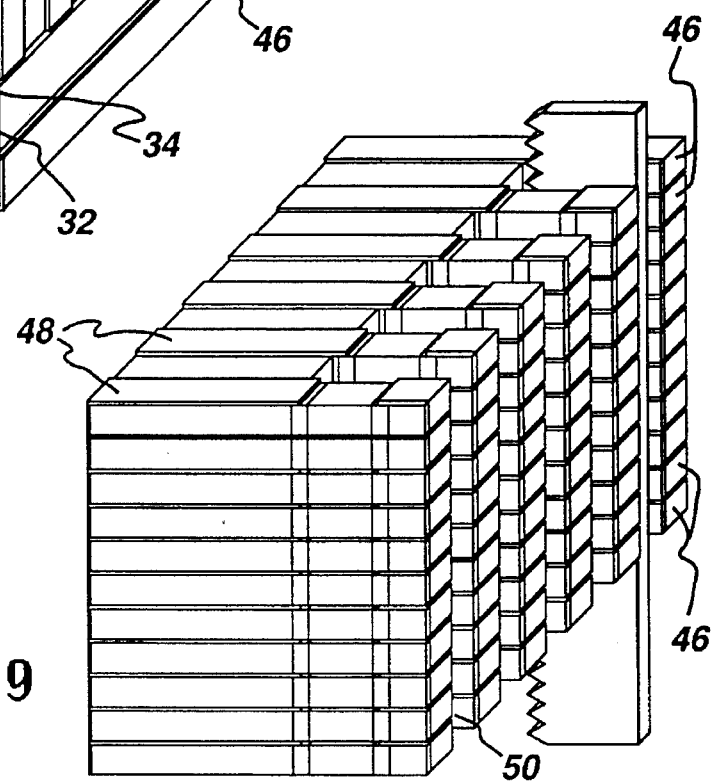
FIG. 9 is an isometric view schematically showing saw kerfs being formed in the assembled transducer block of FIG. 8.

After the conductive metal films 46, 48 are deposited on each of the transducer strips 42, the strips are reassembled in a block form as shown in FIG. 8 and, as shown in FIG. 9, a plurality of equally spaced saw kerfs or grooves 50 are formed in the block perpendicular to the layers in the block and perpendicular to the direction of the original cuts. The grooves 50 extend through the metal films 46, the matching layers 40 and 36, the piezoelectric layers 32, inner backing layers 36, and part way only through the outer lossy backing layers 38. Grooves 50, schematically shown in FIG. 9 as being formed by the saw blade 44, are formed at locations to extend between adjacent conductive metal films 48 and to divide the conductive films 46 into equal parts along the length of the respective transducer strips 42 to thereby form a plurality of spaced transducer elements 52 along the length of each transducer strip 42.

Figure 10:
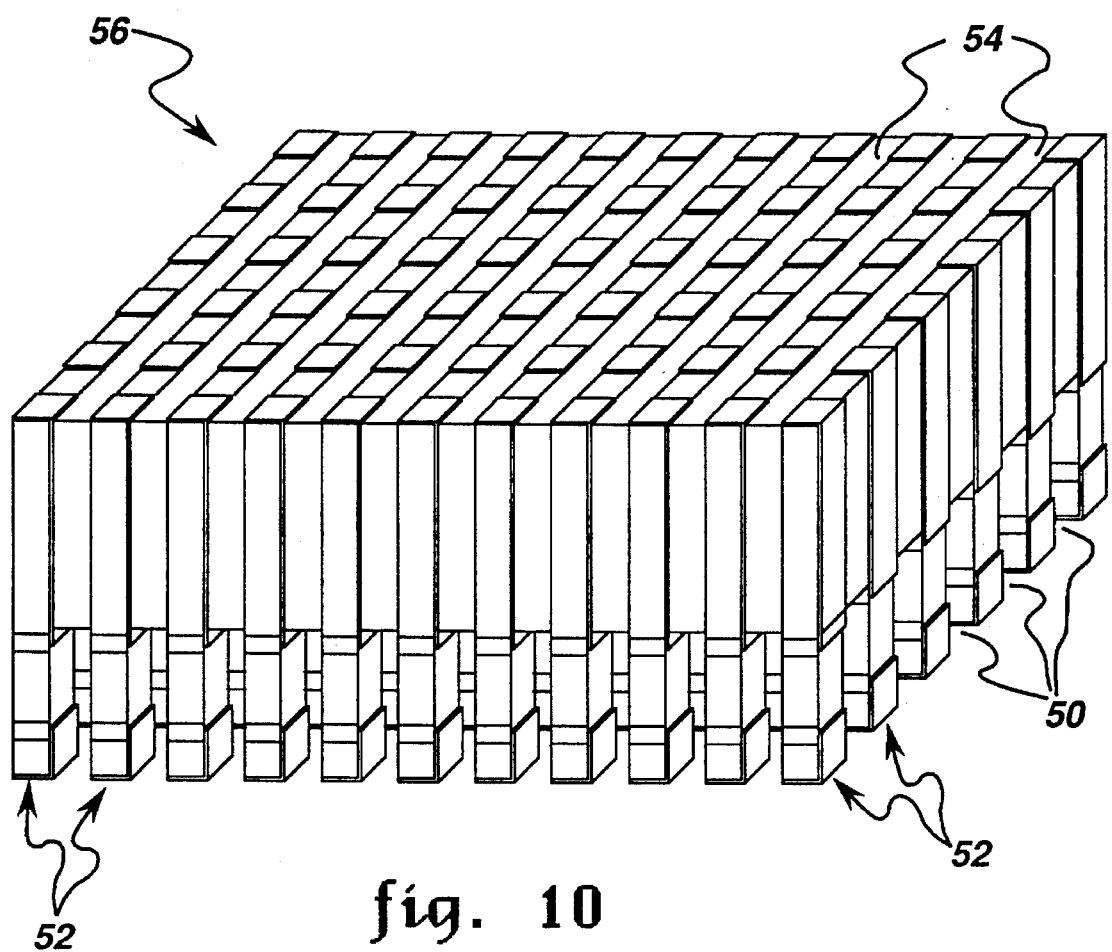
FIG. 10 is an isometric view showing the transducer strips, with the saw kerfs formed therein, assembled in a two-dimensional transducer array.
Figure 11:
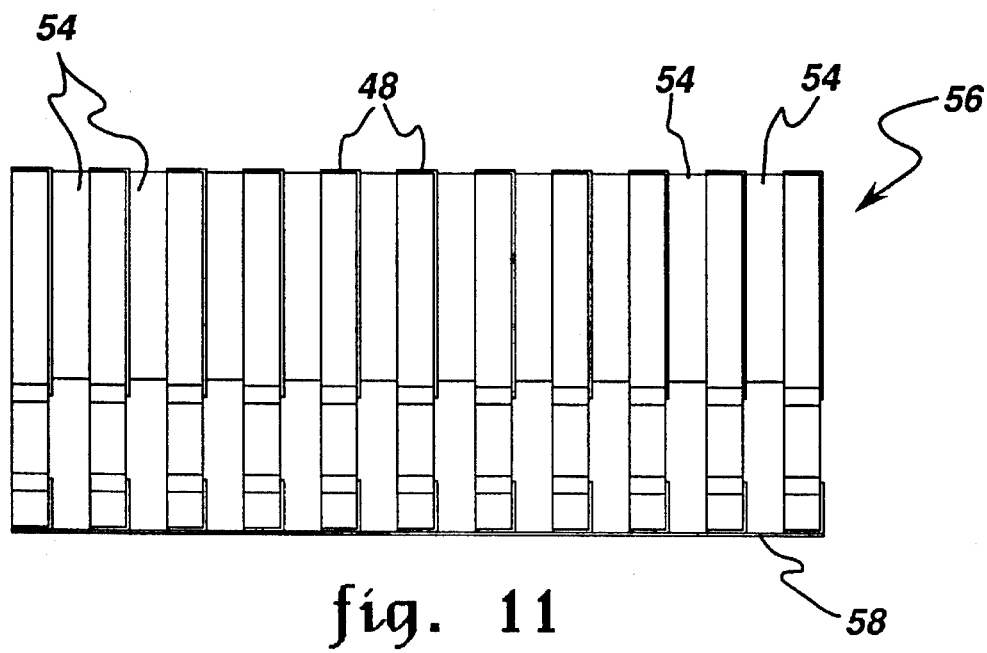
FIG. 11 is an elevation view of the two-dimensional array shown in FIG. 10 and having a conducting film attached to and covering the front surface of the transducer assembly.

As shown in FIG. 10, the transducer strips 42 are then separated and reassembled with electrically insulating spacing members 54 bonded therebetween to form a two-dimensional transducer array 56 in which the individual transducer elements 52 are separated from each adjacent transducer element by an air gap equal to the width of the grooves 50 to provide isolation for all the transducer elements in the array.

As an alternative, the transducer strips with the conducting films deposited thereon may be assembled and bonded into their final, spaced relation prior to forming the grooves 50.

An electric circuit may be provided to each transducer 54 in the array 56 through the conducting metal film elements on the front and back surfaces, respectively, of the outer matching layer 40 and outer backing layer 38 for that transducer element. It is conventional for the front face of a transducer array to be held at ground potential and for the back face of the transducer elements to be independently driven to focus or steer the beam. In the present case, electrical contact to the front surface of the two-dimensional array 56 may be provided by attaching a thin metallized membrane 58 to the front surface of the matching layer to provide electrical contact with all of the transducer elements 56 in the array. An additional advantage of this arrangement is that the metallized film element 58 serves to keep water or other fluids or foreign matter out of the air space isolating the individual transducer elements.

Electrical contact to the back of the individual piezoelectric elements is made by bonding a conductive element to the isolated patches of the metal films 48 on the back surface of the lossy backing layer 38. This may be achieved by any suitable means but preferably the array is attached to a printed circuit board which may have electrical components for driving the array elements to provide the desired two-dimensional steering and focusing of the beam.

By providing a plurality of elongated transducer strips 42 and forming the conductor films 46, 48 on the strips before the individual transducer elements are separated, the film forming step is greatly simplified. Further, since a plurality of individual transducer elements 54 are supported in fixed, spaced relation on a common lossy backing layer strip, assembly of the transducer array is greatly facilitated. The resulting two-dimensional transducer array is very stable and reliable, and substantially more economical than known two-dimensional transducer arrays.

While a preferred method of producing a two-dimensional transducer array and the two-dimensional transducer array provided thereby has been disclosed and described, it should be apparent that the invention is not so limited, and it is intended to include all embodiments which would be apparent to one skilled in the art and which come within the spirit and scope of the invention.

What is claimed is:
1. In a process for producing a two-dimensional ultrasonic transducer array including a plurality of transducer elements arranged in each of a plurality of rows extending in spaced, side-by-side relation with the transducer elements in each row being spaced from one another, the improvement comprising:

forming a plurality of like elongated transducer strips each including a layer of piezoelectric material having a front face and a back surface, a first matching layer formed from an electrically conductive material mounted on and in electrical contact with the front face of the layer of piezoelectric material and a second matching layer of nonconductive material mounted on said first matching layer, a first backing layer of electrically conductive material mounted on and in electrical contact with the back surface of said piezoelectric material and a second backing layer of nonconducting lossy material mounted on said first backing layer, depositing a continuous electrically conducting film on the front surface and one side surface of said second matching layer and into electrical contact with said first matching layer of each said elongated transducer strip to provide electrical contact with the front face of said layer of piezoelectric material through said electrically conductive matching layer, forming a plurality of electrically conducting film strips each extending transversely across the back surface and one side surface of said second backing layer and into electrical contact with one side edge surface, said first backing layer of each said elongated transducer strip to provide electrical contact with the back surface of said layer of piezoelectric material, said electrically conductive film strips being equally spaced along the length of each said elongated transducer strip, forming a plurality of equally spaced grooves in the front face of each said elongated transducer strip, said grooves extending in a plane perpendicular to said layers and transversely of said elongated transducer strips and extending through said continuous electrically conducting film, said matching layers, said piezoelectric layer, and said first backing layer, and into but not through said lossy backing layer, said grooves extending between adjacent electrically conductive film strips to thereby produce a plurality of like ultrasonic transducer elements spaced along the length of said each elongated transducer strip, and mounting said plurality of elongated transducer strips in spaced, parallel, electrically insulated relation to one another to thereby provide a two-dimensional ultrasonic transducer array with each transducer element in the array having means for providing electrical connection from the front and back surfaces of the array to the piezoelectric layer independently of each other transducer element in the array.

2. The process defined in claim 1 wherein said electrically conducting films are metallic films formed on said matching layer surfaces and said backing layer surfaces.

3. The process defined in claim 2 wherein said metallic films are formed by vapor deposition.

4. The process defined in claim 2 wherein said metallic films are formed by ion sputtering.

5. The process defined in claim 2 wherein said metallic films are formed by electrolysis plating.

6. The process defined in claim 2 wherein said metallic films are formed by electroless plating.

7. The process defined in claim 1 wherein said plurality of elongated transducer strips are formed by initially forming transducer block, and sawing the block in parallel, equally spaced planes perpendicular to said layers to form a plurality of equal sized strips.

8. The process defined in claim 1 wherein said first matching layer is a layer of metal.

9. The process defined in claim 1 wherein said matching layer and said first backing layer are metal layers.

10. The process defined in claim 9 wherein said plurality of elongated transducer strips are formed by initially forming a transducer block, and sawing the block in parallel, equally spaced planes perpendicular to said layers to form a plurality of equal sized strips.

11. The process defined in claim 10 wherein said electrically conducting films are metallic films deposited on said matching layer surfaces and said backing layer surfaces.

* * * * *